(12) United States Patent
Zhang et al.

(10) Patent No.: US 11,369,602 B2
(45) Date of Patent: Jun. 28, 2022

(54) USE OF TADALAFIL AS PROTEIN ARGININE METHYLTRANSFERASE (PRMT5) INHIBITOR

(71) Applicant: Fourth Mil. Med. Univ. of People's Lib. Army, Xi'an (CN)

(72) Inventors: Jian Zhang, Xi'an (CN); Ying Wu, Xi'an (CN); Rui Ling, Xi'an (CN); Suning Chen, Xi'an (CN); Lu Han, Xi'an (CN); Wenxia Zhou, Xi'an (CN)

(73) Assignee: Fourth Military Medical University of People's Liberation Army, Xi'an (CN)

( * ) Notice: Subject to any disclaimer, the term of this patent is extended or adjusted under 35 U.S.C. 154(b) by 191 days.

(21) Appl. No.: 16/945,907

(22) Filed: Aug. 2, 2020

(65) Prior Publication Data
US 2021/0052581 A1 Feb. 25, 2021

(30) Foreign Application Priority Data
Aug. 20, 2019 (CN) .......................... 201910770579.2

(51) Int. Cl.
| | | |
|---|---|---|
| C07D 487/14 | (2006.01) |
| A61K 31/4985 | (2006.01) |
| A61P 35/00 | (2006.01) |
| A61K 9/00 | (2006.01) |
| A61K 31/7048 | (2006.01) |

(52) U.S. Cl.
CPC ........ *A61K 31/4985* (2013.01); *A61K 9/0053* (2013.01); *A61P 35/00* (2018.01); *A61K 31/7048* (2013.01)

(58) Field of Classification Search
CPC ..................................................... C07D 487/14
USPC ........................................................ 544/343
See application file for complete search history.

*Primary Examiner* — Douglas M Willis
(74) *Attorney, Agent, or Firm* — Weide & Miller, Ltd.

(57) ABSTRACT

The present invention provides use of Tadalafil as a protein arginine methyltransferase 5 (PRMT5) inhibitor. The present invention finds out that Tadalafil is a PRMT5 inhibitor by virtually screening active compounds targeting PRMT5 based on crystal structure and information about active sites of PRMT5. The present invention not only confirms that Tadalafil can inhibit an enzymatic activity of PRMT5, but also confirms that Tadalafil alone can inhibit tumor growth in breast cancer and improve sensitivity to chemotherapy for breast cancer.

7 Claims, 4 Drawing Sheets

USE OF TADALAFIL AS PROTEIN ARGININE METHYLTRANSFERASE (PRMT5) INHIBITOR

RELATED APPLICATION DATA

This application claims priority benefit of Chinese Patent Application No. 201910770579.2 (CN), filed Aug. 20, 2019, the contents of the said prior application is incorporated by reference as if set forth in its entirety herein.

FIELD OF THE INVENTION

The present invention relates to the mechanism of improved sensitivity to chemotherapy with Doxorubicin by Tadalafil, in particular to use of Tadalafil as an inhibitor targeting protein arginine methyltransferase 5 (PRMT5) in breast cancer treatment.

BACKGROUND OF THE INVENTION

In the field of computer aided drug design (CADD), it is very important to accurately understand the interaction between a target protein and an active molecule. For this end, progress in X-ray diffraction technology for biomacromolecules provides many structures of proteins and nucleic acid molecules. These structures can act as targets for bioactive substances and help people understand the mechanisms of biological actions of active substances. The general principle for CADD is known as obtaining a structure of a binding site of a receptor macromolecule by single-crystal X-ray diffraction, and using a molecular simulation software to analyze the structural properties of the binding site, for example, electrostatic fields, hydrophobic fields, and distribution of hydrogen bonding sites; then searching a database or using molecular drug design technology to recognize and obtain a molecule whose molecular shape and physical and chemical properties matches an active site of the receptor, followed by synthesizing the molecule and testing biological activities thereof, repeating the operations for several rounds, and finally and possibly, finding a potential lead compound.

PRMTs are a class of catalytic enzymes catalyzing active methyl to transfer to an arginine residue of a protein. PRMTs modify substrates by methylation, which changes structures and stabilities of target proteins, and enables the function of repairing DNA damage and the like. There are 9 human PRMTs members which can be divided into three types dependent on methylation types: monomethylation (MMA), symmetric dimethylation (SDMA) and asymmetric dimethylation (ADMA). Type I and type II PRMTs are relatively important. PRMT5 is a type II PRMT catalyzing MMA and SDMA. A large number of studies show that, PRMT5 is highly expressed in a variety of cancer tissues and closely relates to poor prognosis. Previous studies from applicant's group show that PRMT5 can promote DNA repair in breast cancer and its high expression may result in drug resistance in Doxorubicin treatment. Thus, inhibition of PRMT5 function can facilitate improvement of sensitivity to Doxorubicin treatment and the effect of adjuvant chemotherapy.

Since PRMT5 plays an important role in a process of tumorigenesis, design of a small molecule inhibitor against PRMT5 has become a hotspot in research and development of anti-tumor drugs. Combination of CADD with chemical synthesis of drugs helps to obtain a small molecule inhibitor having a strong activity and certain selectivity for PRMT5. Currently, reported PRMT5 inhibitors include JNJ-64619178, EPZ015666, GSK3326595 and the like, where only GSK3326595 (EPZ015938) and JNJ-64619178 have entered clinical trial phases. There have been some studies on PRMT5 inhibitors, but a certain period of time is needed for clinical trials based on the current study results, and it needs a relatively long time to see whether an inhibitor can proceed for clinical application. Screening of PRMT5 inhibitors using commercially available small molecules can greatly shorten a research period and accelerates transformation from basic research to clinical trial.

Tadalafil has a molecular formula of $C_{22}H_{19}N_3O_4$ which is a selective and reversible inhibitor of cyclic guanosine monophosphate (cGMP)-specific phosphodiesterase 5 (PDE5). At present, Tadalafil is mainly used to treat men with erectile dysfunction. Clinical research shows that Tadalafil can increase the anti-hypertensive effect of a nitrate drug. It is regarded as the results of the nitrate drug and Tadalafil acting together on nitric oxide/cGMP pathway. Tadalafil is not used for women currently, thus there is no study of Tadalafil in pregnant women. Animal experiments do not show Tadalafil is harmful to pregnancy, embryo/fetus development or postnatal development directly or indirectly. Pharmacokinetics of Tadalafil in healthy subjects shows a linear relationship between time and dose.

Liu Jinjin et al. (Reversal of Doxorubicin resistance in MCF-7/ADR cells by Vardenafil) mention Vardenafil, Sildenafil and Tadalafil reversing Doxorubicin resistance in MCF-7/ADR cells and analyze a mechanism from apoptosis aspect, but do not reveal Tadalafil as a PRMT5 inhibitor.

SUMMARY OF THE INVENTION

An objective of the present invention is to provide use of Tadalafil as a PRMT5 inhibitor.

In order to achieve the above objective, the present invention adopts the following technical solutions.

Use of Tadalafil in preparation of a drug used for treating a tumor by inhibiting the enzymatic activity of PRMT5.

Use of Tadalafil in preparation of a drug used for treating breast cancer.

Use of Tadalafil in preparation of a drug used for inhibiting proliferation of breast cancer cells.

Use of Tadalafil in preparation of a drug used for adjuvant chemotherapy for breast cancer.

Preferably, the drug is an oral preparation.

Preferably, Tadalafil is administered in 1.29-2.58 mg/kg (for mouse), corresponding to an oral administration of 10-20 mg for human (calculated with 70 kg body weight).

The present invention has the following beneficial effects:

The present invention finds out that Tadalafil is a PRMT5 inhibitor by virtually screening active compounds targeting PRMT5 based on crystal structure and active sites of PRMT5. The present invention confirms that Tadalafil can inhibit the enzymatic activity of PRMT5. The present invention also confirms that Tadalafil alone can inhibit tumor growth in breast cancer by chemotherapy sensitivity test and interference test using an ordinary breast cancer cell line and a xenograft tumor-bearing animal model. Moreover, Tadalafil has a PRMT5 inhibitory activity which is advantageous in prevention of occurrence of drug resistance in treatment of breast cancer with Doxorubicin, and which improves sensitivity to chemotherapy for breast cancer.

DETAILED DESCRIPTION OF THE INVENTION

The present invention is further described in detail below with reference to the accompanying drawings and examples.

1. Screen of PRMT5 Inhibitors

Crystal structural data of PRMT5 was downloaded from PDB database with PDB ID: 3UA4. It represented structure of PRMT5 without a ligand.

Structural data of marketed small molecule drugs was obtained by sorting out and summarizing public data, including structural information of 1813 approved small molecule drugs for clinical use.

In silico virtual screening includes the following steps:

(1) establishment of three-dimensional structure of a small molecule: using babel command to convert SDF provided with a marketed drug into three-dimensional PDB format. A babel command was used to convert an SDF document into smi string and then into a PDB document. During conversion from smi to PDB structure, babel created a non-planar molecular stereostructure based on characteristics of atomic connections.

(2) molecular docking simulation: using AutoDock Vina for molecular docking. The small molecule was constrained for docking within an effective binding space based on its crystal structure. Vina deduced change of binding free energy of the small molecule by calculating intermolecular interaction forces such as hydrogen bond and charge interaction between a molecule in a grid and the crystal structure, and searched for a best docking position by simulated annealing algorithm. Vina achieved semi-flexible docking by identifying rotatable bonds of the small molecule based on atomic connections of the small molecule. Nine searches were performed after calculation and finally gave docking conformations. The present screen used the crystal structure of PDB ID: 3UA4 as a docking object. Based on information about active sites of the structure provided by literature, a cubic zone centered (72.75, −1.427, 13.062) with side length of 30 was used for search.

Figure 1:
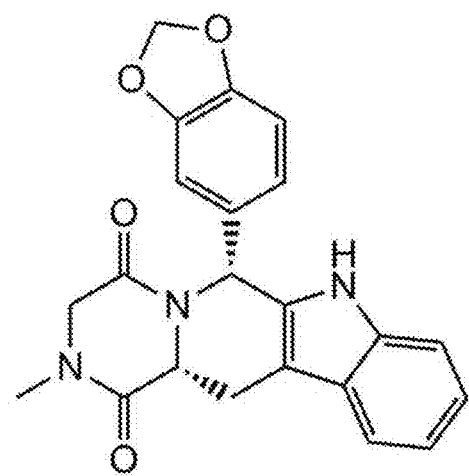
FIG. 1 is a schematic diagram of a molecular structure of Tadalafil.
Figure 2:
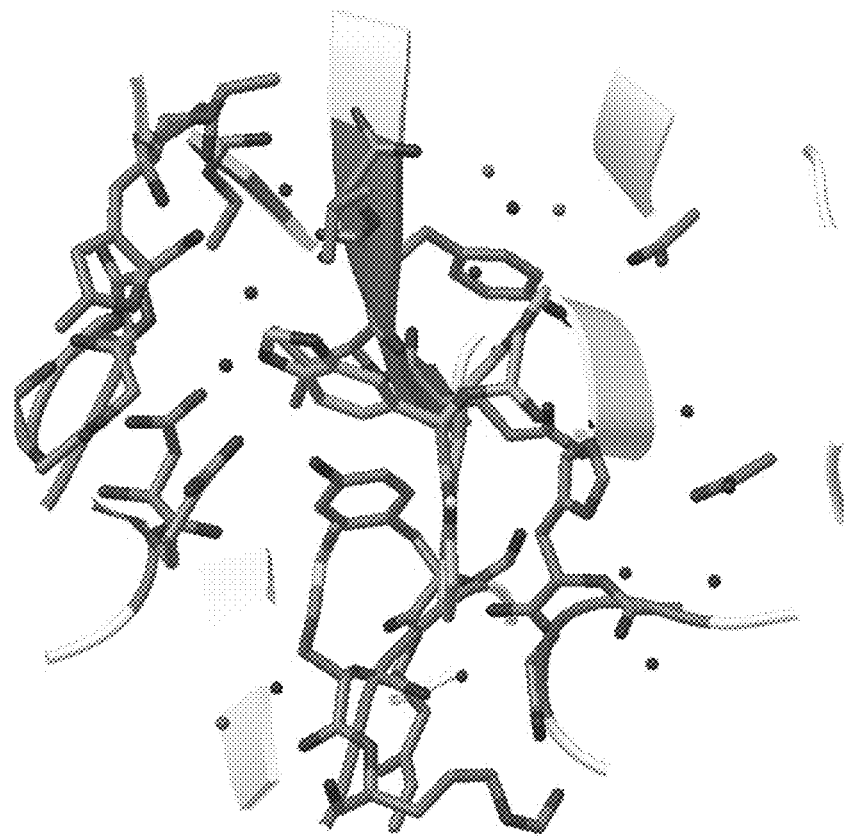
FIG. 2 is a schematic diagram showing a conformation of PRMT5 binding Tadalafil around the active sites of the protein crystal structure.

(3) screen of candidate drugs: based on docking score of <−8.0 and molecular weight of <400, Tadalafil (molecular weight of 389.4) and Sulfasalazine (molecular weight of 398.39) were screened out from a marketed drug library. The molecular structure of Tadalafil was shown in FIG. 1, and the best binding conformation for docking thereof with PRMT5 (3UA4) was shown in FIG. 2. However, later functional experiment and SPR experiment showed that, Sulfasalazine had a relatively weak tumor inhibitory effect and lower binding ability to PRMT5.

2. Analysis of Affinity of Tadalafil for PRMT5

Figure 3:
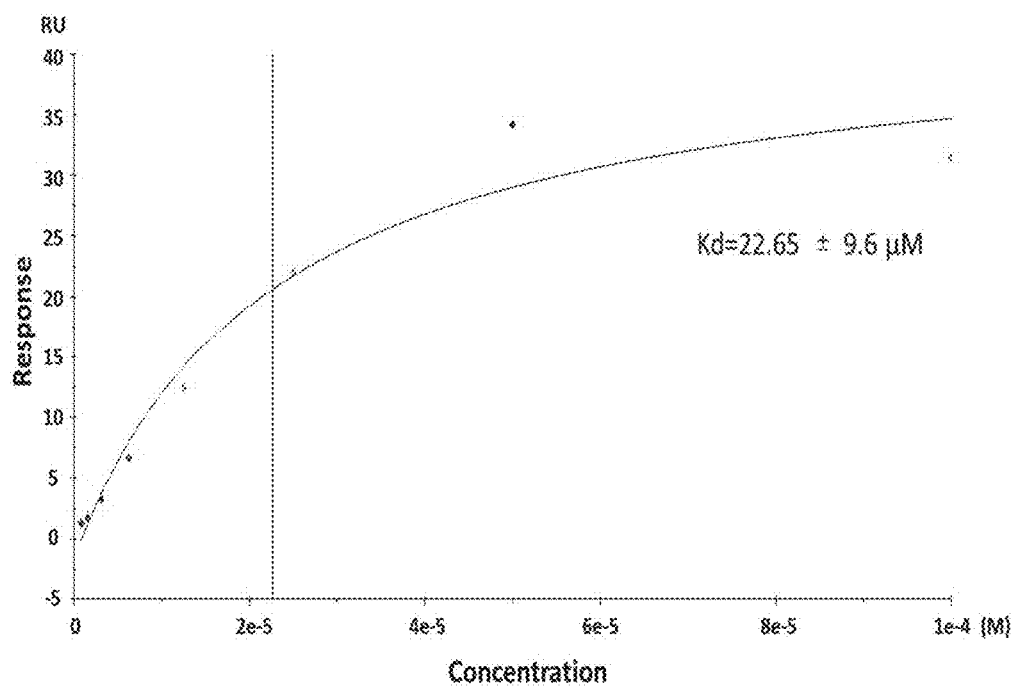
FIG. 3 is a schematic diagram showing the affinity of Tadalafil for PRMT5 (results of surface plasmon resonance (SPR) analysis).

Analysis of affinity of Tadalafil for target protein (PRMT5) was carried out using Biacore T200 analysis platform and SPR technology. Tadalafil was obtained from MCE corporation with catalog no: HY-9 0009A (50 mg). PRMT5/MEP50 purified protein was obtained from abcam corporation with catalog no: ab198151 (20 μg). Tadalafil was diluted to a series of concentrations in sequence of: 0.78, 1.56, 3.125, 6.25, 12.5, 25, 50 and 100 (μM). Results in FIG. 3 showed that, Tadalafil has a relatively desirable affinity for PRMT5 with $K_d$=22.65±9.6 μM.

3. Analysis of Tadalafil Inhibiting the Enzymatic Function of PRMT5

Figure 4:
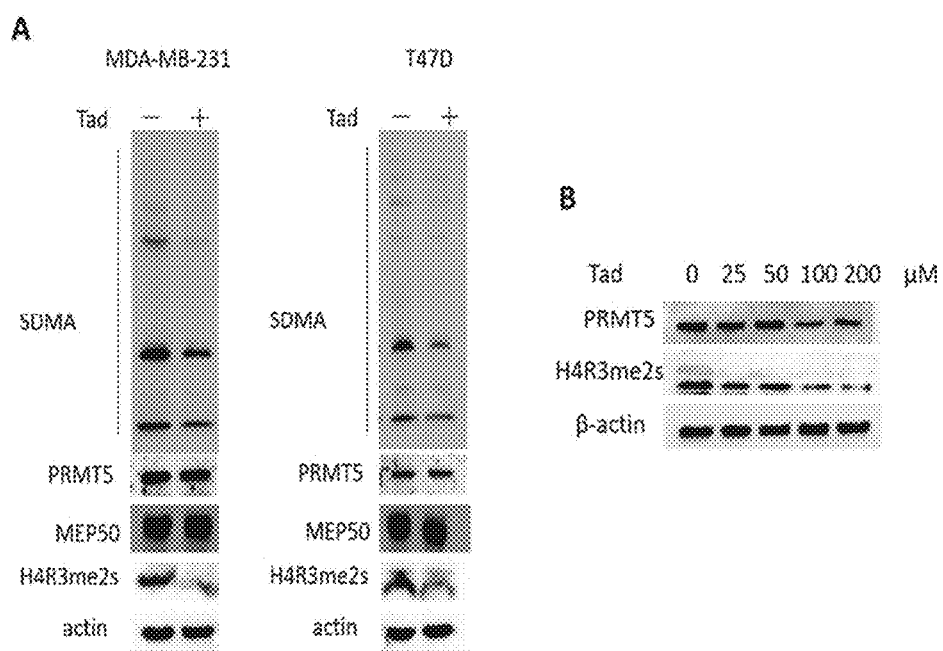
FIG. 4 is a schematic diagram showing Tadalafil inhibiting an enzymatic function of PRMT5 and levels of downstream substrates: (A) expression of PRMT5 downstream substrates SDMA (Symmetric Di-Methyl Arginine) and H4R3me2s, with Tad (i.e. Tadalafil) 100 μM, 24 h; (B) expression of PRMT5 downstream substrates SDMA and H4R3me2s at different concentrations of Tadalafil; actin is an internal control; MEP50 is a protein for stable binding to PRMT5 to exhibit the function of PRMT5, and used as an internal control.

Tadalafil was applied to MDA-MB-231 and T47D cells respectively, and the expression levels of PRMT5, H4R3me2s (downstream substrate of PRMT5) and SDMA were measured. Western blot results showed that, the expression levels of downstream substrates H4R3me2s and SDMA were significantly decreased (FIG. 4A) while the expression levels of PRMT5 and its downstream substrate H4R3me2s were inhibited by Tadalafil in a dose dependent manner (FIG. 4B). These results demonstrated that, Tadalafil can inhibit the enzymatic activity of PRMT5.

4. Tadalafil in Combination with Doxorubicin Improving Sensitivity to Chemotherapy for Breast Cancer (at Cellular Level)

Figure 5:
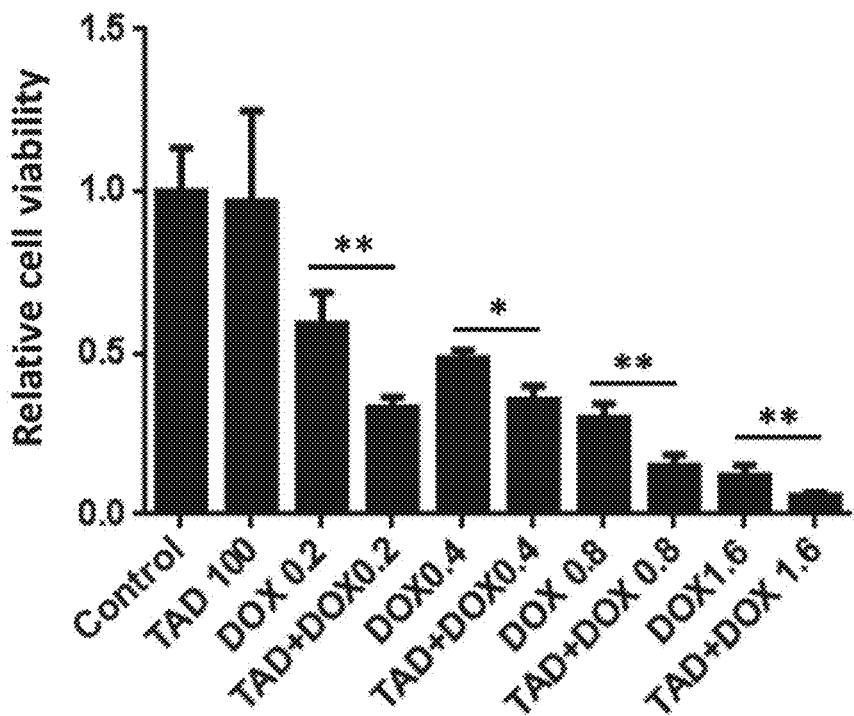
FIG. 5 is a schematic diagram showing synergy of Tadalafil and Doxorubicin improving sensitivity to chemotherapy for breast cancer (cell proliferation assay), with Tadalafil (Tad)100 μM; Doxorubicin (DOX): 0.2, 0.4, 0.8, 1.6 μg/mL; *p<0.05, **p<0.01.

Multiple group experiment was carried out using Tadalafil (100 μM) in combination with different concentrations of Doxorubicin (0, 0.2, 0.4, 0.8, 1.60 μg/mL) acting on breast cancer cells of MDA-MB-231, corresponding to groups of TAD 100, TAD+DOX 0.2, TAD+DOX 0.4, TAD+DOX 0.8, and TAD+DOX 1.6. A negative control group underwent PBS treatment while positive control groups were treated with Doxorubicin alone with corresponding concentrations (DOX 0.2, DOX 0.4, DOX 0.8, and DOX 1.6). Results of cell proliferation assay (MTT) after 48 hours from drug administration showed that, Tadalafil significantly increased sensitivity of the breast cancer cells to Doxorubicin in a short time (FIG. 5).

5. Tadalafil in Combination with Doxorubicin Improving Sensitivity to Chemotherapy for Breast Cancer (at Animal Level)

Figure 6:
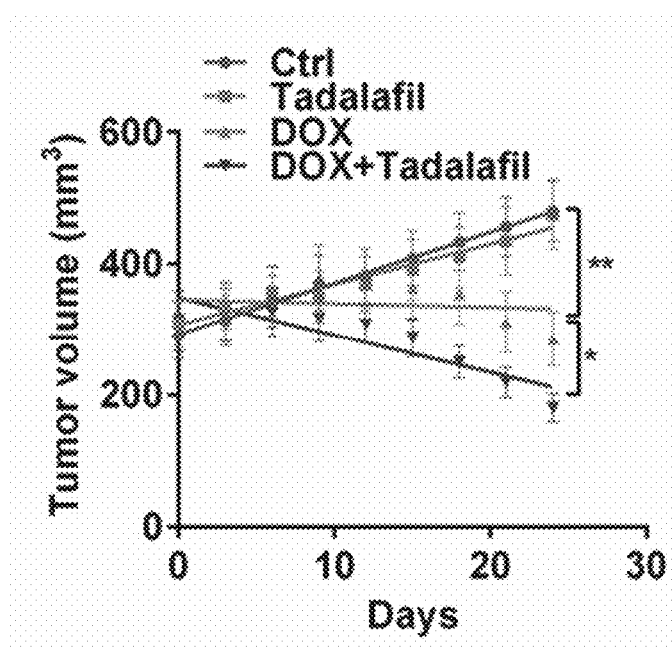
FIG. 6 is a schematic diagram showing interference by Tadalafil and synergy of Tadalafil and Doxorubicin improving sensitivity to chemotherapy for breast cancer (in vivo functional analysis in PDX (Patient-Derived Xenograft) mice model).
Figure 7:
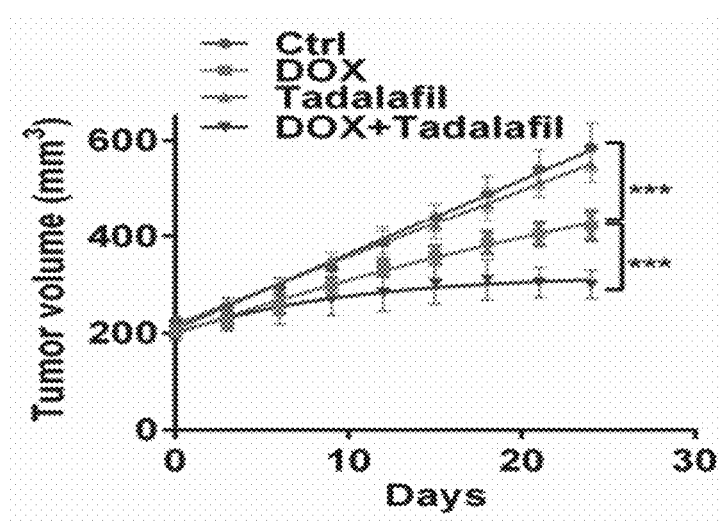
FIG. 7 depicts the data and results from a study showing the combination of Tadalafil with Doxorubicin as inhibiting breast tumor growth (using the PDX (Patient-Derived Xenograft) mice model).

Immunodeficient mice were seeded with MDA-MB-231 cells respectively. When tumor volumes reached 50-100 mm3, mice were given treatment selected from the following: PBS (Control, Ctrl), Tadalafil, Doxorubicin (DOX), Tadalafil in combination with Doxorubicin (DOX+Tadalafil). Tadalafil was administered by oral gavage (2 mg/kg, once a day) while Doxorubicin was administered by mouse tail vein injection (2 mg/kg, once a week). Body weights of mice and tumor volumes were measured every day for 25 days. Results showed that mouse tumor volume in the control group kept increasing, groups with Tadalafil alone and with Doxorubicin alone inhibited tumor growth, and mouse tumor volume in the group with Tadalafil in combination with Doxorubicin was significantly reduced (FIG. 6). The results demonstrated that Tadalafil alone (administration frequency increased comparing to Tadalafil in combination with Doxorubicin) or in combination with Doxorubicin can be used to treat breast cancer; Tadalafil in combination with Doxorubicin can improve the treatment effect of chemotherapy for breast cancer (improved treatment effect indicating that Tadalafil can improve sensitivity to chemotherapy for breast cancer through combination with Doxorubicin by inhibiting the enzymatic activity of PRMT5). This result was further confirmed by additional studies of Tadalafil in combination with Doxorubicin demonstrating, using a PDX (Patient-Derived tumor Xenograft) model, that this combination inhibited tumor grown (FIG. 7).

What is claimed is:

1. A method for treating a tumor in a patient, wherein the method comprises administering to the patient in need thereof a therapeutically effective amount of Tadalafil;
   wherein the treatment of the tumor in the patient occurs by inhibiting protein arginine methyltransferase 5 (PRMT5) activity in the patient.

2. The method of claim 1, wherein the tumor is a breast cancer tumor.

3. The method of claim 2, wherein the administration is oral.

4. A method for inhibiting proliferation of breast cancer cells in a patient, wherein the method comprises administering to the patient in need thereof a therapeutically effective amount of Tadalafil;
   wherein the inhibition of the proliferation of breast cancer cells in the patient occurs by inhibiting protein arginine methyltransferase 5 (PRMT5) activity in the patient.

5. The method of claim 4, wherein the method further comprises administering to the patient in need thereof a therapeutically effective amount of Doxorubicin.

6. The method of claim 5, wherein the administration is simultaneous or sequential.

7. The method of claim 6, wherein the administration is oral.

* * * * *